(12) United States Patent
Groenland et al.

(10) Patent No.: US 11,684,342 B2
(45) Date of Patent: Jun. 27, 2023

(54) INTRAVASCULAR ULTRASOUND IMAGING

(71) Applicant: KONINKLIJKE PHILIPS N.V., Eindhoven (NL)

(72) Inventors: Alfons Wouter Groenland, Best (NL); Alberto Fazzi, Eindhoven (NL); Cesar Perez, Roseville, CA (US); Asher Cohen, San Francisco, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 0 days.

(21) Appl. No.: 16/487,240

(22) PCT Filed: Dec. 2, 2018

(86) PCT No.: PCT/EP2018/053373
§ 371 (c)(1),
(2) Date: Aug. 20, 2019

(87) PCT Pub. No.: WO2018/158064
PCT Pub. Date: Sep. 7, 2018

(65) Prior Publication Data
US 2021/0128109 A1 May 6, 2021

Related U.S. Application Data

(60) Provisional application No. 62/464,804, filed on Feb. 28, 2017.

(30) Foreign Application Priority Data

Mar. 17, 2017 (EP) .................................... 17161491

(51) Int. Cl.
*A61B 8/00* (2006.01)
*A61B 8/08* (2006.01)
(Continued)

(52) U.S. Cl.
CPC .......... *A61B 8/445* (2013.01); *A61B 1/00004* (2013.01); *A61B 1/00114* (2013.01);
(Continued)

(58) Field of Classification Search
CPC . A61B 8/445; A61B 1/00004; A61B 1/00114; A61B 1/00124; A61B 1/00128; A61B 8/0891; A61B 8/12; A61B 8/56
See application file for complete search history.

(56) References Cited

U.S. PATENT DOCUMENTS 6,251,078 B1 6/2001 Moore
2004/0049321 A1* 3/2004 Lehr ........................ G06F 1/26
700/286

(Continued)

FOREIGN PATENT DOCUMENTS

EP 1063500 A2 12/2000
JP 7280624 A 10/1995
(Continued)

OTHER PUBLICATIONS

Sweet S., How can a splitter also be a combiner? (2018), The Solid Signal Blog: https://blog.solidsignal.com/tutorials/how-can-a-splitter-also-be-a-combiner/. (Year: 2018).*

(Continued)

*Primary Examiner* — Joseph M Santos Rodriguez
*Assistant Examiner* — Kaitlyn E Sebastian

(57) ABSTRACT

An extension cable is adapted for use in an intravascular ultrasound system. It has a first connector, for connecting to a catheter and a second connector for connecting to a patient interface module. A cable arrangement provides power transmission, data transmission and data signal processing (amplification or regeneration) between the first and second connectors. The extension cable enables sterility to be maintained in a workflow in a time efficient and easy manner (Continued)

as the catheter to extension cable connection may remain in a sterile environment.

12 Claims, 4 Drawing Sheets

(51) Int. Cl.
    *A61B 1/00*         (2006.01)
    *A61B 8/12*         (2006.01)

(52) U.S. Cl.
    CPC ...... *A61B 1/00124* (2013.01); *A61B 1/00128* (2013.01); *A61B 8/0891* (2013.01); *A61B 8/12* (2013.01)

(56) References Cited

U.S. PATENT DOCUMENTS

| | | | |
|---|---|---|---|
| 2006/0184035 A1* | 8/2006 | Kimura | A61B 8/4488 600/466 |
| 2007/0237468 A1* | 10/2007 | Aronson | G02B 6/3817 385/100 |
| 2008/0146940 A1* | 6/2008 | Jenkins | A61B 8/4422 600/463 |
| 2011/0092833 A1 | 4/2011 | Farrior | |
| 2012/0177087 A1* | 7/2012 | Konishi | H04L 5/14 375/219 |
| 2013/0146326 A1* | 6/2013 | Gundel | H01B 7/0823 174/102 R |
| 2014/0343434 A1 | 11/2014 | Elbert | |
| 2015/0190610 A1 | 7/2015 | Lichtenstein et al. | |
| 2015/0272538 A1* | 10/2015 | Millett | A61B 5/026 600/301 |
| 2016/0166327 A1 | 6/2016 | Keller | |
| 2016/0243334 A1* | 8/2016 | Da Silva | A61M 39/16 |
| 2018/0296114 A1* | 10/2018 | Welsh | A61B 5/283 |
| 2018/0360417 A1* | 12/2018 | Henneken | A61B 8/445 |

FOREIGN PATENT DOCUMENTS

| | | | | |
|---|---|---|---|---|
| JP | 2002051999 A | | 2/2002 | |
| WO | 2000061007 A1 | | 10/2000 | |
| WO | WO-0061007 A1 | * | 10/2000 | ............... A61B 8/12 |
| WO | 2014072891 A1 | | 5/2014 | |

OTHER PUBLICATIONS

International Search Report and Written Opinion, International Application No. PCT/EP2018/053373, dated May 14, 2018.

* cited by examiner

INTRAVASCULAR ULTRASOUND IMAGING

CROSS-REFERENCE TO PRIOR APPLICATIONS

This application is the U.S. National Phase application under 35 U.S.C. § 371 of International Application No. PCT/EP2018/053373, filed on 2 Dec. 2018, which claims the benefit of U.S. Provisional Patent Application No. 62/464804, filed on 28 Feb. 2017 and European Patent Application No. 17161491.0, filed on 17 Mar. 2017. These applications are hereby incorporated by reference herein.

FIELD OF THE INVENTION

This invention relates to apparatus for intravascular ultrasound (IVUS) imaging, for example inside a living body.

BACKGROUND OF THE INVENTION

Intravascular ultrasound (IVUS) imaging is widely used in interventional cardiology as a diagnostic tool for a diseased vessel, such as an artery, within the human body to determine the need for treatment, to guide the intervention, and/or to assess its effectiveness.

To perform an IVUS imaging study, an IVUS catheter that incorporates one or more ultrasound transducers is passed into the vessel and guided to the area to be imaged. The transducers emit and receive ultrasonic energy in order to create an image of the vessel of interest. Ultrasonic waves are partially reflected by discontinuities arising from tissue structures (such as the various layers of the vessel wall), red blood cells, and other features of interest. Echoes from the reflected waves are received by a transducer and passed along to an IVUS imaging system, which is connected to the IVUS catheter by way of a patient interface module (PIM). The imaging system processes the received ultrasound signals to produce a cross-sectional image of the vessel where the device is placed.

There are two types of IVUS catheters commonly in use today: rotational and solid-state. For a typical rotational IVUS catheter, a single ultrasound transducer element is located at the tip of a flexible driveshaft that spins inside a plastic sheath inserted into the vessel of interest. The transducer element is oriented such that the ultrasound beam propagates generally perpendicular to the axis of the device. The fluid-filled sheath protects the vessel tissue from the spinning transducer and driveshaft while permitting ultrasound signals to propagate from the transducer into the tissue and back. As the driveshaft rotates, the transducer is periodically excited with a high voltage pulse to emit a short burst of ultrasound. The same transducer then listens for the returning echoes reflected from various tissue structures. The IVUS imaging system assembles a two dimensional display of the vessel cross-section from a sequence of pulse/acquisition cycles occurring during a single revolution of the transducer.

In contrast, solid-state IVUS catheters carry an ultrasound probe assembly that includes an array of ultrasound transducers distributed around the circumference of the device connected to a set of transducer control circuits. The transducer control circuits select individual transducers for transmitting an ultrasound pulse and for receiving the echo signal. By stepping through a sequence of transmitter-receiver pairs, the solid-state IVUS system can synthesize the effect of a mechanically scanned transducer element but without moving parts. Since there is no rotating mechanical element, the transducer array can be placed in direct contact with the blood and vessel tissue with minimal risk of vessel trauma. Furthermore, because there is no rotating element, the interface is simplified. The solid-state probe can be wired directly to the imaging system with a simple electrical cable and a standard detachable electrical connector.

A number of electrical conductors or wires extend along the length of the device to facilitate the communication of signals to and from the ultrasound transducer(s). For example, in some current commercial products seven wires extend along the length of the catheter between a proximal connector and the ultrasound assembly at the distal portion of the catheter.

Intravascular ultrasound procedures are carried out in special surgery rooms (so-called "cathlabs" which include other modalities (interventional X-ray, transdermal ultrasound etc.). The IVUS systems can be integrated or cart-based. In both cases, the catheter is plugged into the patient interface module (PIM). The PIM is typically mounted to the side bedrail and connected with a cable to the backend system. To minimize clutter, the PIM position is fixed and cables are often hidden below or into the table. Apart from galvanic isolation and electrical buffering of signals, the PIM is a mechanical anchor to secure the patient against accidental cable pulls on the PIM (people stumbling upon the cable, or a sudden cart movement for instance).

In a variety of procedures, vascular access from various vessels is required with different access locations across the body. Often the upper leg (femoral access) or lower arm (radial access) are used. The PIM is mounted permanently on the table side, and it is located at the boundary of the non-sterile zone, as close as possible to commonly used vascular access locations.

For a procedure, the sterile IVUS catheter is plugged into the PIM with a 1.5 m cable that is part of the catheter assembly. By doing so, the connector of the catheter becomes non-sterile, since the PIM is at or outside the sterile area boundary. This prohibits temporal disconnection and storage of the catheter in the sterile field to make room for other instruments during the procedure, which is a frequent requirement of physicians.

For most procedures, the location of the PIM is not ideal: it is located at the very edge of the sterile field, resulting from the combination of preferred vascular access locations and limited catheter cable length. To keep the PIM sterile, it needs to be covered with a sterile drape that easily moves away or has to be moved during the intervention. This area of the table (typically halfway up the patient's body) is crowded with many instruments during the procedure. The ideal position of the PIM would be at the footboard of the bed. Here, there is much more space available and the edge of the sterile zone is much further away (e.g. at least 50 cm), making the drape much more robust against position movements. With no other instruments present in this area, only accidental drape moves are likely to occur.

In some cases, due to the variety of procedures, and patient dimensions particularly for obese patients, the 1.5 m catheter cable length is simply insufficient to reach the preferred vascular access position, even from the position half way up the bed. In practice, physicians then decouple the PIM from the side bedrail and place it on top of the patient. As it is now located in the sterile zone; they pack it in sterile shields. This is also needed for the cable between the PIM and the backend. Packing this cable is a clumsy business, requiring a sterile and non-sterile nurse to fit a 5 m cable in a cable shaped sterile pouch without breaking the sterility; a job that severely impacts the workflow and that needs to be avoided, if possible.

Furthermore, by detaching the PIM from the bedrail, the mechanical anchoring function has disappeared, thereby putting patient safety at risk.

There is a need for an IVUS system which addresses these issues.

SUMMARY OF THE INVENTION

The invention is defined by the claims.

According to examples in accordance with an aspect of the invention, there is provided an extension cable adapted for use in an intravascular ultrasound system, comprising:

a first connector, for electrical and mechanical connection to an intravascular ultrasound catheter;

a second connector, for electrical and mechanical connection to an intravascular ultrasound patient interface module; and a cable arrangement for power transmission and data transmission, and a signal processor, between the first and second connectors.

This extension cable is adapted for use between an ultrasound catheter and a patient interface module. It enables sterility to be maintained in a workflow in a time efficient and easy manner, while also providing mechanical anchoring. In particular, the catheter can remain in a sterile area, and the extension cable instead crosses the sterile boundary. Thus, the catheter may be disconnected from the extension cable and reconnected without compromising sterility. The catheter may for example be disconnected in the sterile field enabling temporal storage of the catheter in a different location.

The extension cable also allows more design freedom in the cable between the PIM and the backend. In particular, the extension cable enables the maximum length between the patient and the PIM to be increased. For example, a PIM with digital output, high speed digital connections and with a power supply function in a single electrical cable may be limited to 3 m in practice, whereas a cable length up to 5 m may be preferred for a mobile IVUS system. By enabling greater cable lengths between the catheter and the PIM, the PIM may be positioned closer to the mobile IVUS backend system (where the signal processing takes place) enabling the use of shorter PIM-backend interconnect cables, in particular by extending the patient-PIM (catheter-side) cable rather than the PIM-backend (backend side) cable.

The signal processor may comprise an electrical buffer with gain 1 or an electrical amplifier with gain greater than 1, and the cable arrangement comprises an electrical cable for both power transmission and data transmission. This provides an all-electrical solution, wherein the cable arrangement relays electrical signals between the catheter and the patient interface module.

The signal processor is for example located at the first connector end of the electrical cable. Thus, it provides signal amplification or buffering of the catheter signals as soon as they are received.

The signal processor may comprise a first electrical amplifier located at the first connector end of the electrical cable and a second electrical amplifier located at the second connector end of the electrical cable. This may further improve signal amplification and also be used to provide impedance matching. An impedance matching circuit may also be provided.

The cable arrangement may in general carry at least power signals and data signals, wherein the signal processor is arranged for processing the data signals.

In general, only the data signals require amplification (or buffering); the power signals do not. Hence, this embodiment provides the advantage that signal processing (i.e. buffering or amplification) resources are efficiently directed only the signals that are in need of amplification, and not to those which are not. This improves efficiency of signal processing in the cable.

In one electrical arrangement, the cable arrangement comprises a set of parallel electrical lines forming an electrical power transmission cable and an electrical data transmission cable in parallel, wherein the signal processor is provided along the electrical lines of the data transmission cable. The electrical power transmission cable may carry power signals; the electrical data transmission cable may carry data signals.

There may thus be multiple electrical lines, such as data, power, control and ground, and the signal processing (buffering or amplification) is provide for the data lines. This, inter alia, improves efficiency of signal processing, as described above.

In another electrical arrangement, the cable arrangement comprises a combined electrical cable which carries superposed power and data signals, wherein the extension cable further comprises a splitter for extracting the data signals and a combiner for recombining the data signals with the power signals, wherein the signal processor is provided for the extracted data signals.

This reduces the number of electrical lines needed in the cable arrangement. Signal processing (i.e. buffering or amplification) is applied to the data signals. Hence this arrangement advantageously reduces the number of lines needed in the cable arrangement, reducing cost and bulk, while at the same time ensuring that signal processing resources (i.e. amplification or buffering) remain directed only to processing of the signals which truly require amplification (i.e. the data signals).

The cable arrangement may be a hybrid electrical and optical arrangement. For example, the cable arrangement may comprise an optical fiber for the data transmission and an electrical cable for the power transmission, and wherein the signal processor comprises an electrical-to-optical converter. The signal processor then provides signal shaping and quality improvement as part of the electrical-to-optical conversion, rather than by electrical amplification.

The optical signals at the output of the fiber may be provided directly to the PIM if it includes the required optical to electrical conversion. Alternatively, the signal processor may further comprise an optical to electrical converter, with the electrical-to-optical converter and the optical to electrical converter at opposite ends of the optical fiber. The extension cable then presents an electrical output which is equivalent to the electrical input received from the catheter.

The cable arrangement may instead be an essentially optical arrangement. The cable arrangement for example may comprise an optical fiber, and wherein the signal processor comprises a combiner for combining data signals with power signals, an electrical-to-optical converter for providing the combined signals to the optical fiber for the power transmission and the data transmission, an optical to electrical converter, and a splitter for extracting the data signals and the power signals. In this way, the extension cable further provides optical power transfer.

The extension cable may include a dedicated power line, for powering the signal processor, which extends along the extension cable from the first and/or second connectors. The power supply between the catheter and the PIM is then not interrupted, and the extension cable may simply function as a power line connector.

Alternatively, a coupling may be provided to a power transmission line of the cable arrangement. In this way, power is tapped from the existing power line, to supply the signal processor.

In another arrangement, an embedded power source is provided for the signal processor.

The extension cable may have a length between 1 m and 5 m. This is sufficient to provide flexibility for the positioning of the PIM while maintaining the connection between the extension cable and the catheter in the sterile area.

The invention also provides an intravascular ultrasound system, comprising:
a catheter having an ultrasound probe at its tip;
a patient interface module; and
an extension cable as defined above for coupling between the catheter and the patient interface module.

The patient interface module then connects to a backend system (console) via another cable.

BRIEF DESCRIPTION OF THE DRAWINGS

Examples of the invention will now be described in detail with reference to the accompanying drawings, in which.

DETAILED DESCRIPTION OF THE EMBODIMENTS

The invention provides an extension cable which is adapted for use in an intravascular ultrasound system. It has a first connector, for connecting to a catheter and a second connector for connecting to a patient interface module. A cable arrangement provides power transmission, data transmission and data signal processing (amplification or regeneration) between the first and second connectors. The extension cable enables sterility to be maintained in a workflow in a time efficient and easy manner as the catheter to extension cable connection may remain in a sterile environment.

Figure 1:
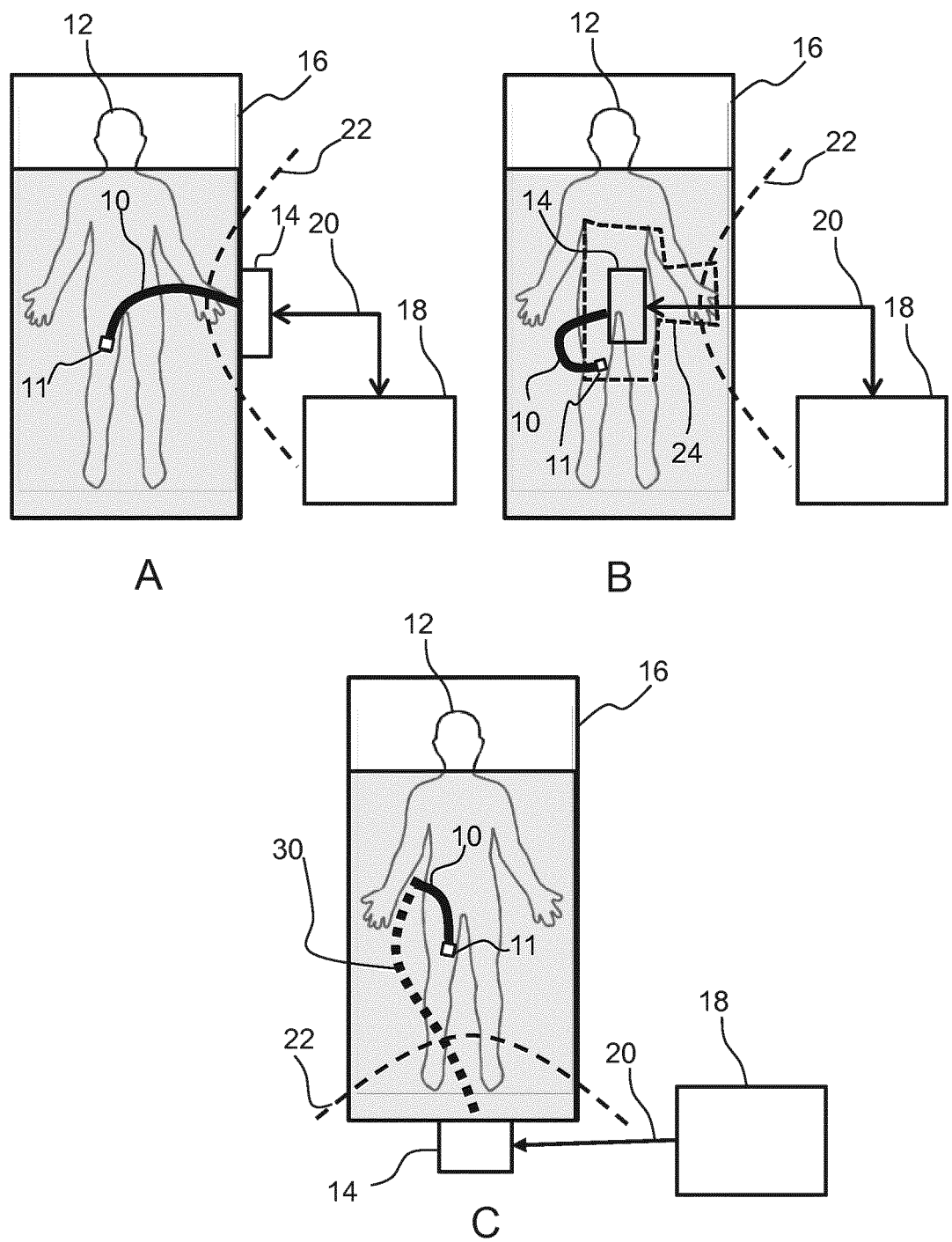
FIG. 1A shows a typical arrangement of an ultrasound catheter which enters the upper leg of a patient.
FIG. 1B shows that the short catheter length means that a physician may sometimes place the PIM on the patient.
FIG. 1C shows the arrangement enabled by an extension cable of the invention.

FIG. 1A shows a typical arrangement of an ultrasound catheter 10 which enters the upper leg of a patient 12. The catheter has an ultrasound probe 11 at its tip. The catheter 10 connects to a patient interface module (PIM) 14 which is attached to a side rail of the patient bed 16. The PIM connects to a back-end processor 18 by electrical cable 20. The line 22 represents the boundary between the sterile environment and the non-sterile environment.

FIG. 1B shows that the short catheter length (typically 1.5 m) means that physician may sometimes place the PIM 14 on the patient to bring it nearer to the catheter entry point. As the PIM is moved from the non-sterile environment, it has to be encased in a sterile pouch 24.

FIG. 1C shows the arrangement enabled by an extension cable of the invention. The extension cable 30 is active, in that it includes signal processing. It is placed between the catheter 10 and the PIM 14. By doing so, the PIM can be positioned at the footboard of the bed, at the same position for all procedures and at more substantial distance from the edge 22 of the sterile field.

The active signal processing within the extension cable 30 enables the IVUS catheter to maintain signal integrity. The extension cable 30 is sterile by itself, similar to the catheter, so there is no need to put a sterile pouch around it. It can be disposable (like the catheter), or it may be a cable which can be sterilized.

Moreover, the connection between the catheter 10 and the extension cable 30 is located in the sterile field, so that it is possible to temporarily unplug the catheter and store it at some other place without compromising sterility.

A typical length of the extension cable is 3 m, but it can be longer or shorter, for example in the range 1 m to 5 m.

Figure 2:
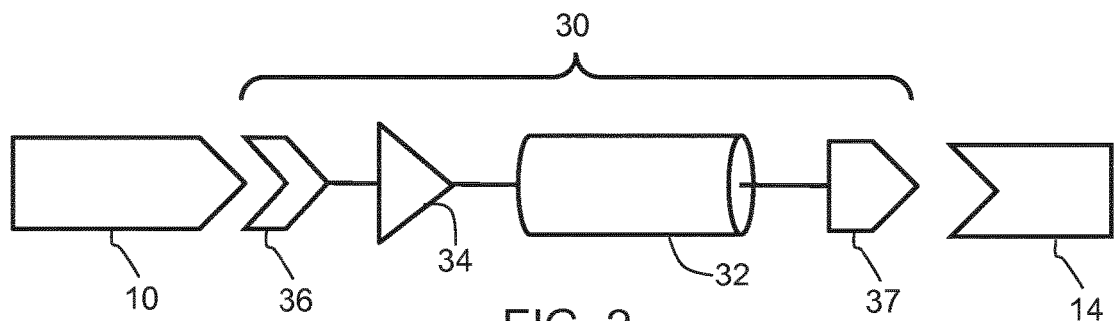
FIG. 2 shows the general architecture of the active extension cable between the ultrasound catheter and the PIM.

FIG. 2 shows the general architecture of the active extension cable 30 between the ultrasound catheter 10 and the PIM 14.

It consists of a cable arrangement 32, capable of transferring the signals of interest (from the catheter and towards the catheter), a signal processor 34 to compensate for signal quality losses resulting from the extension cable, and connectors. A first connector 36 is for connecting to the catheter 10 and a second connector 37 is for connecting to the PIM 14. The connectors may correspond to the existing PIM and catheter connectors, so that the connector 36 is the same as the connection port of the PIM and the connector 37 is that same as the connection port of the catheter. The two connectors thus have opposite gender so one connector is male (which may be considered to be a connector) and the other is female (which may be considered to be a receptor). Any arbitrary combination of genders can be used, as long as the extension cable can be inserted between the catheter and PIM without further additions.

As will be discussed below, the extension cable may be entirely electrical, or else it may include an optical signal transmission medium, namely an optical fiber. The electrical implementation will first be described.

The signal processor for an electrical implementation comprises an amplifier. The amplifier may have a gain 1 so that it functions only as a signal regenerating buffer, or else it may have a higher amplification. The term "amplifier" should be understood accordingly. In addition to adding gain or providing signal regeneration, the signal processor may also be used as impedance transformation unit, to match the impedance to the desired level. In general, cabling in a radio frequency based system is designed to have a specific impedance (50 or 75 Ohms typically) for optimal signal transfer.

The amplifier or buffer implements this impedance matching to take account of the additional cable length introduced by the extension cable, and it has impedance matching circuitry for this purpose. The amplifier secures signal integrity over the additional cable length.

For the intravascular ultrasound application, the connector 37 at the PIM side needs to have an Ingress Protection (IP) greater than level 4 against moisture for safe operation. For the connector 36 at the catheter side, located on top of the patient during the procedure, a higher IP rating might be required, for example level 7 or greater to enable immersion in liquid.

The amplifier 34 may be positioned anywhere in the cable. However, placing it closest to the catheter, for example as part of the connector 36 will enable the least influence of the extension cable on the signal quality.

The electrical signals provided by the transducer element of the catheter typically have a frequency content in the range of 10-30 MHz (plus higher harmonics). As a result of the micro coaxial cables and connectors used in existing catheters, the current 1.5 m catheter cable is at its length limit as a result of parasitic electrical components. A passive extension cable would lower the bandwidth below the acceptable limit.

Figure 3:
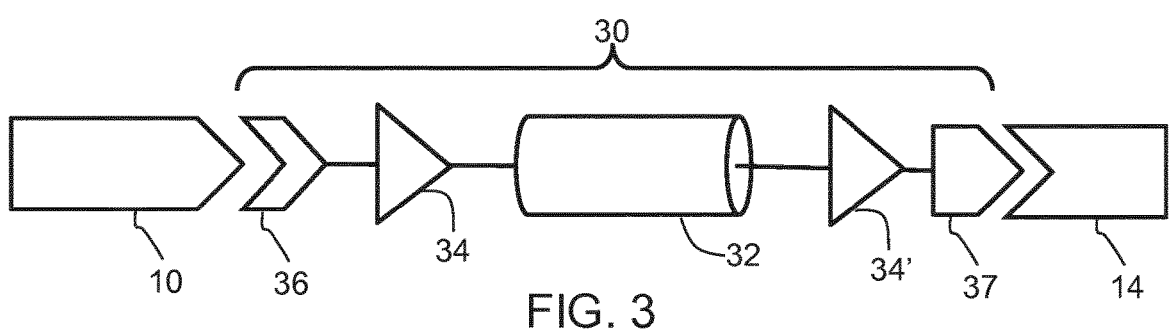
FIG. 3 shows a system with two amplifiers.

FIG. 3 shows that a second amplifier 34' may be provided at the second connector end to further improve signal quality and impedance matching. All examples described below with signal buffering or amplification at the first connector end may be extended with further signal buffering or amplification at the second connector end.

The amplifier is an active block that requires power to operate.

Figure 4:
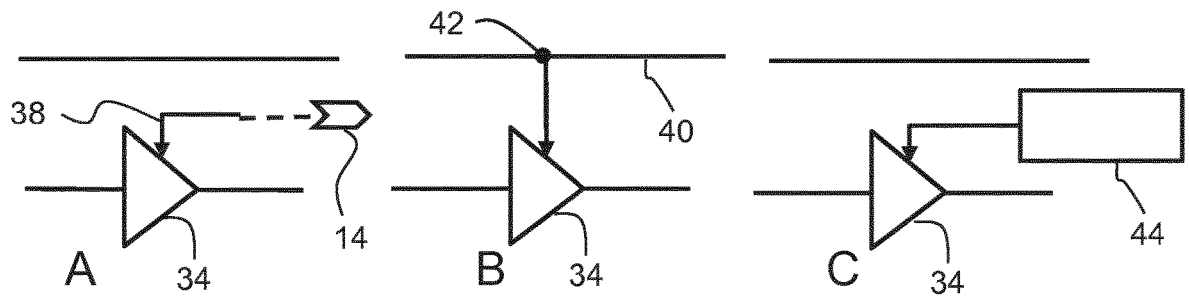
FIG. 4A shows the amplifier powered by a dedicated power line from the PIM.
FIG. 4B shows a first alternative which is backward compatible using an existing power line.
FIG. 4C shows a second alternative which is backward compatible using an embedded power source.

FIG. 4 shows possible ways to power the amplifier (and other signal processing functions).

FIG. 4A shows the amplifier 34 powered by a dedicated power line 38 from the PIM 14. This dedicated additional power line is not a feature of current PIMs so would be implemented with a new PIM. The additional power line 38 may instead be provided from the catheter side (even though the original power supply is at the PIM). However, the extension cable does not require modification to the catheter or to existing PIMs.

FIG. 4B shows a first alternative which is backward compatible. The catheter is an active device which itself is powered by the PIM, so the extension cable is already providing power between the PIM and the catheter. For example, the extension cable includes a power line 40, and the extension cable can draw power from the catheter power line 40, by having a coupling 42 to the power line. This is possible by ensuring the power consumption of the amplifier 34 is small and the power supply has enough headroom to accommodate for this extra power without compromising on catheter functionality.

FIG. 4C shows a second alternative which is backward compatible. The extension cable has embedded power source 44 for the signal amplifier 34. The embedded power source 44 may comprise a battery or a super-capacitor embedded in the extension cable. This arrangement can be used to minimize noise and distortion added by the amplifier or when the catheter power supply does not allow for tapping of power.

In FIG. 4, a single signal line is shown. Of course, there may be single or multiple lines.

All examples described below are shown based on power being tapped from the existing power line of the extension cable as shown in FIG. 4B. However, they may be adapted to make use of dedicated power lines or an embedded power supply.

The signals extending along the extension cable and thereby the wires in the cable itself can be arranged in various configurations. Signals can be split among a number of wires (in parallel) or can be super positioned on a single wire pair.

Figure 5:
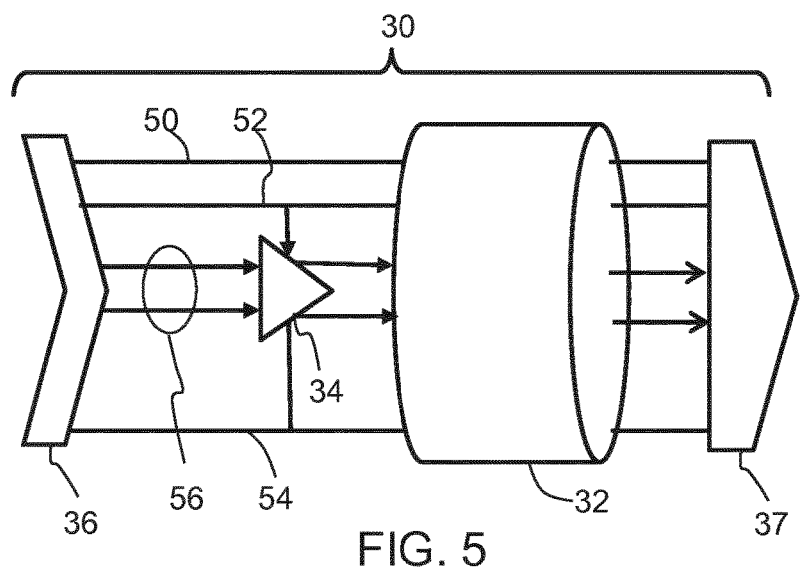
FIG. 5 shows an example of the electrical signals output by the catheter and hence needing to be extended by the extension cable.

FIG. 5 shows an example of the electrical signals output by the catheter and hence needing to be extended by the extension cable 30 for an all-electrical implementation with parallel signal lines.

The signals comprise a control signal or set of control signals carried on a control line 50. The control signals control signals for example provide error messages, warnings, clock signals, trigger signals etc. The control line 50 may be a single line or multiple lines for the different types of control signal.

A high power rail is carried on a power line 52, a ground signal is carried on a ground line 54 and a set of parallel data lines 56 provide the data signals. The cable is thus a multi-core cable, to provide the functions of control, triggers, clock, power, data and ground (for shielding). Signals can run over more than one wire in parallel such as the high and low power lines, and data can be provided as single ended or differentially coded. The data signals are received echo signals.

In general, the data signals need amplification whereas the control signals do not as they are far less sensitive to noise. However, any signals may be chosen to be amplified or otherwise processed by the signal processor. In FIG. 5, only the data lines 56 are provided to the signal processor, but this is simply an example.

Figure 6:
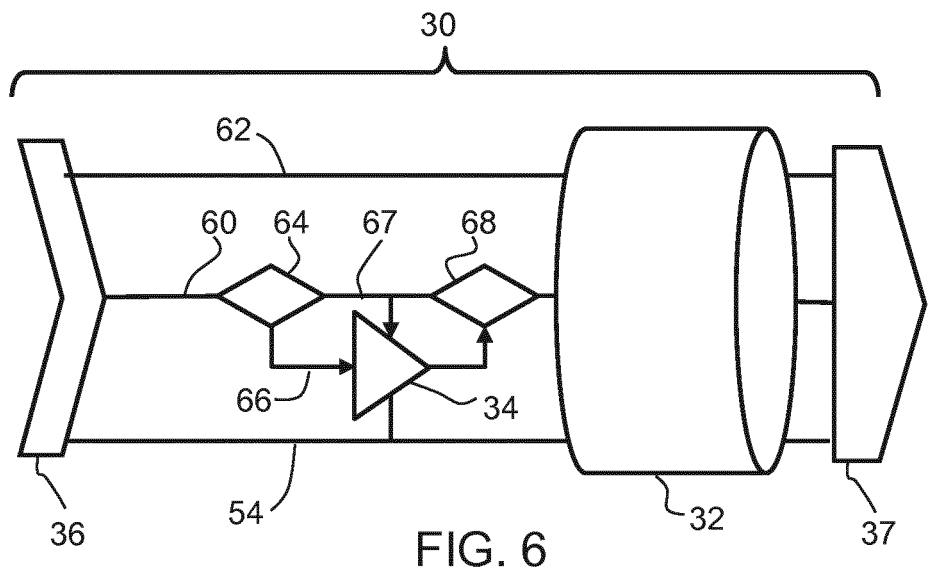
FIG. 6 shows an example of the electrical signals output by the catheter with superposition of data and power transmission.

FIG. 6 shows an example of the electrical signals output by the catheter and hence needing to be extended by the extension cable 30 for an all-electrical implementation with superposition of data and power transmission.

The power and data are combined on a single bus 60, optionally accompanied by a separate control line or lines 62. FIG. 6 shows a splitter 64 for extracting the data signals 66 and passing forward the power signals 67, and a combiner 68 for recombining the data signals 66 after amplification or buffering with the power signals 67.

In this way, the power and data signals are split. This may for example make use of a cross-over network in case of AC/DC superposition. Power is shown as drawn from the power signals 67 to power the signal processor 34. A ground line again is shown as 54 which runs alongside the fiber.

Figure 7:
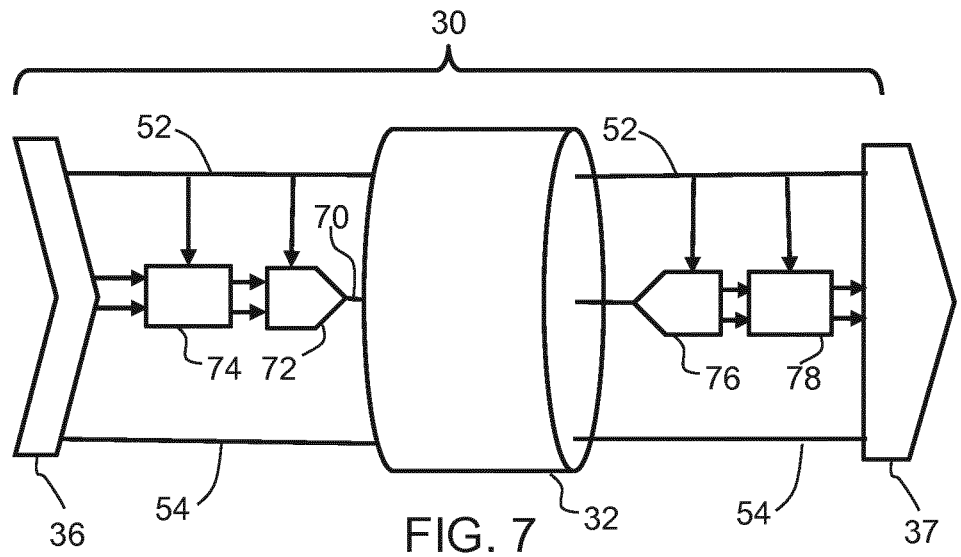
FIG. 7 shows a hybrid design in which electrical power lines are provided as well an optical fiber for carrying the data.

FIG. 7 shows a hybrid design in which electrical power lines (power rail 52 and ground 54) are provided as well an optical fiber 70 for carrying the data.

The data is not electrically amplified, but converted into the optical domain using an electrical-to-optical converter 72. There is also optionally electrical signal processing in unit 74 if required before electrical-to-optical conversion.

After the transmission along the extension cable, there is conversion back into the electrical domain using an optical to electrical converter 76 and optionally electrical signal processing in unit 78. The signal processing for example comprises analog to digital conversion at the catheter end, and digital to analogue conversion at the PIM end. The signal processing may also include impedance matching.

Optical data transfer is known to have very low losses. The optical encoder for electrical-to-optical conversion may be implemented as any high speed light source, such as an LED or vertical cavity surface emitting laser (VCSEL). Both can be made power efficient and small enough to fit into the connector. The control signals and power in this example remain in the electrical domain and are fed with the optical fiber into a hybrid cable 32.

Figure 8:
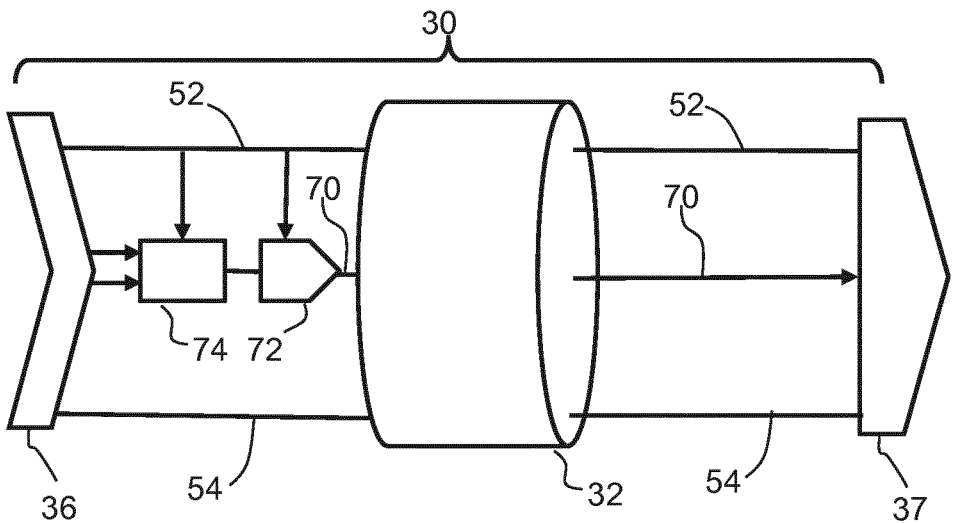
FIG. 8 shows another variation in which the optical fiber signals are provided directly to the PIM.

FIG. 8 shows another variation in which the optical fiber signals are provided directly to the PIM. This may be possible for a digital PIM which is able to receive the digital optical signal directly.

Figure 9:
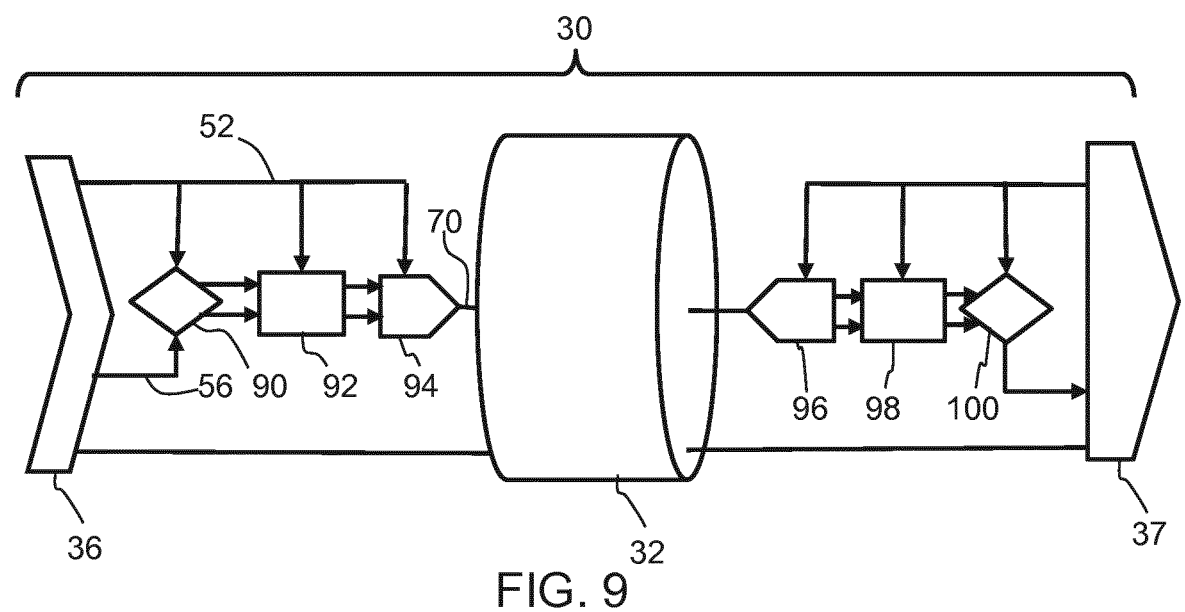
FIG. 9 shows another variation which is essentially all-optical.

In addition to a hybrid electrical-optical system, a system which is essentially all-optical is also possible as shown in FIG. 9.

The power line 52 and data line (or lines) 56 are provided to a combiner 90. The combined signals are then processed in a processing unit 92 and converted to optical signals by electrical to optical converter 94.

The ground line 54 remains an electrical line.

After transmission over the optical fiber 70 there is optical to electrical conversion in optical to electrical converter 96, signal processing in unit 98 and then splitting in splitter 100 to create the required set of electrical inputs to the PIM.

The control signals and power signal in this example are optical as well as the data signal, and are fed with the optical fiber into a hybrid cable 32 (which includes the electrical ground connection).

Optical power transfer is for example described in WO 2014072891 A1 and is a promising technology for catheters.

The ultrasound probe carried by the catheter may for example comprise piezoelectric zirconate transducer (PZT) solid-state transducers, capacitive micro-machined ultrasonic transducers (CMUTs), and/or piezoelectric micro-machined ultrasound transducers (PMUTs). The ultrasound system may be rotational or static.

The catheter design has not been described in detail as its design does not need to be changed to implement the invention. The catheter may include an imaging core and an outer catheter/sheath assembly. The backend system 18 for example comprises an imaging system which may be a phased-array ultrasound imaging system.

At a high level, the catheter emits ultrasonic energy from an ultrasound probe at the tip of the device. The ultrasonic energy is reflected by tissue structures surrounding the probe and the echo signals from the tissue are received and amplified by the ultrasound probe. The PIM forwards the received signals and may perform preliminary signal processing prior to transmitting the signals to the back end system (console). The PIM for example performs amplification, filtering, and/or aggregating of the data. The may PIM also supply high- and low-voltage DC power to support operation of the circuitry within the ultrasound probe.

The catheter may include a guide wire exit port to implement a rapid-exchange catheter. The guide wire exit port allows a guide wire to be inserted towards the distal end in order to direct the device through the vessel.

The system may for example be used for imaging the liver, heart, kidneys, gall bladder, pancreas, lungs; ducts; intestines; nervous system structures including the brain, dural sac, spinal cord and peripheral nerves; the urinary tract; as well as valves within the blood or other systems of the body. In addition to imaging natural structures, the images may also include imaging man-made structures such as, but without limitation, heart valves, stents, shunts, filters and other devices positioned within the body. The catheter may also include an inflatable balloon portion near the distal tip The extension cable may be used for any number of wires between the catheter and PIM. One known example is a four-wire system. A low number of wires allows an IVUS catheter to have a better flex radius as it goes through tortuous pathways, and more importantly reduces the risk of broken wire or welds.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. An intravascular ultrasound (IVUS) imaging system, comprising:
   an IVUS catheter comprising:
      an ultrasound probe; and
      a catheter cable;
   an extension cable different than the catheter cable, wherein the extension cable comprises:
      a first connector configured for direct electrical and mechanical connection to the IVUS catheter;
      a second connector opposite to the first connector; and
      a cable arrangement extending between the first connector and the second connector, wherein the cable arrangement is configured for IVUS power transmission and IVUS data transmission, wherein cable arrangement comprises:
         a combined electrical cable configured to carry IVUS power signals and IVUS data signals that are superposed;
         a splitter for extracting the IVUS data signals from the IVUS power signals and IVUS data signals that are superposed;
         a signal processor configured to process the extracted IVUS data signals, wherein the signal processor comprises an electrical buffer with gain 1 or an electrical amplifier with gain greater than 1; and
         a combiner for recombining the processed IVUS data signals with the IVUS power signals.

2. The IVUS system of claim 1, further comprising:
   a patient interface module (PIM), wherein the second connector is configured for direct electrical and mechanical connection to the patient interface module such that the extension cable is the only component positioned between the IVUS catheter and the PIM.

3. The IVUS system of claim 2, wherein the PIM comprises a housing and a connection port configured to connect to the second connector.

4. The IVUS system of claim 3, wherein the PIM comprises at least one of:
   a power supply; or
   a further signal processor.

5. The IVUS system of claim 1,
   wherein the IVUS power signals are different from the IVUS data signals, and
   wherein the IVUS power signals are configured to power at least one of the ultrasound probe or the signal processor.

6. The IVUS system of claim 1, wherein the signal processor is located at the first connector end of the cable arrangement.

7. The IVUS system of claim 1, wherein the signal processor comprises a first electrical amplifier located at the first connector end of the cable arrangement and a second electrical amplifier located at the second connector end of the cable arrangement.

8. The IVUS system of claim 1, wherein the extension cable further comprises an impedance matching circuit.

9. The IVUS system of claim 1, wherein the extension cable further comprises a dedicated power line for powering the signal processor which extends along the extension cable from the first and/or second connectors.

10. The IVUS system of claim 1, wherein the extension cable further comprises a coupling to a power transmission line of the cable arrangement.

11. The IVUS system of claim 1, wherein the extension cable further comprises an embedded power source for the signal processor.

12. The IVUS system of claim 1, wherein the extension cable has a length between 1 m and 5 m.

\* \* \* \* \*